United States Patent
Levin et al.

(10) Patent No.: US 10,820,827 B2
(45) Date of Patent: Nov. 3, 2020

(54) DRY WEIGHT PREDICTOR

(75) Inventors: Nathan W. Levin, New York, NY (US); Fansan Zhu, Flushing, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 886 days.

(21) Appl. No.: 13/879,220

(22) PCT Filed: Oct. 12, 2011

(86) PCT No.: PCT/US2011/055916
§ 371 (c)(1),
(2), (4) Date: Apr. 12, 2013

(87) PCT Pub. No.: WO2012/051261
PCT Pub. Date: Apr. 19, 2012

(65) Prior Publication Data
US 2013/0197389 A1    Aug. 1, 2013

Related U.S. Application Data

(60) Provisional application No. 61/393,544, filed on Oct. 15, 2010.

(51) Int. Cl.
A61B 5/053 (2006.01)
A61B 5/00 (2006.01)
G06F 19/00 (2018.01)

(52) U.S. Cl.
CPC .......... *A61B 5/0537* (2013.01); *A61B 5/6828* (2013.01); *G06F 19/3481* (2013.01)

(58) Field of Classification Search
CPC ...... A61B 5/4869–4881; A61B 5/0537; A61B 5/6828; G06F 19/3481
See application file for complete search history.

(56) References Cited

U.S. PATENT DOCUMENTS

| 3,536,258 A | 10/1970 | Rocheleau |
| 6,615,077 B1 | 9/2003 | Zhu et al. |

(Continued)

FOREIGN PATENT DOCUMENTS

| WO | 2004049938 A1 | 6/2004 |
| WO | WO 2005/027717 | 3/2005 |

(Continued)

OTHER PUBLICATIONS

Duggan, Time to abolish "gold standard" BMJ. Jun. 13, 1992; 304(6841): 1568-1569.*

(Continued)

*Primary Examiner* — David J. McCrosky

(57) ABSTRACT

Methods and apparatus for predicting/estimating the dry weight of an individual, e.g., a patient undergoing dialysis treatment, are provided. The techniques employ a bioimpedance measurement (303) on the individual's calf (101) to obtain information regarding the extracellular fluid volume of the calf. Using a measurement of the calf's circumference (309), a resistivity value is calculated, normalized by the individual's body mass index (BMI), and then offset by a reference value to obtain a new variable, ΔnRho, which is shown, by comparison with a "gold standard" (FIGS. 5-9), to be highly effective in predicting/estimating dry weight (FIGS. 10-13 and 15-16). The techniques are easy to use and provide accurate dry weight predictions/estimations without substantially adding to the complexity or cost of dialysis procedures. The techniques can also be used for individuals who are not renal patients, e.g., patients suffering from other diseases in which fluid overload can occur, athletes, fitness enthusiasts, and the like.

20 Claims, 11 Drawing Sheets

(56) References Cited

U.S. PATENT DOCUMENTS

| | | |
|---|---|---|
| 7,072,710 B2 | 7/2006 | Chamney |
| 7,133,716 B2 | 11/2006 | Kraemer et al. |
| 2006/0122540 A1 | 6/2006 | Zhu et al. |
| 2009/0062728 A1 | 3/2009 | Woo |
| 2009/0062730 A1 | 3/2009 | Woo |

FOREIGN PATENT DOCUMENTS

| | | |
|---|---|---|
| WO | WO 2006/002656 | 1/2006 |
| WO | 2006042218 A2 | 4/2006 |

OTHER PUBLICATIONS

Versi, "Gold standard" is an appropriate term. BMJ. Jul. 18, 1992; 305(6846): 187.*

Wystrychowski, et al. (2007). Dry weight: Sine qua non of adequate dialysis. Advances in Chronic Kidney Disease, 14(3), Abstract.*

Moissl, et al. "Body fluid volume determination via body composition spectroscopy in health and disease." Physiological measurement 27.9 (2006): 921. Retrieved from <stacks.iop.org/PM/27/921> on Oct. 16, 2015.*

Chamney et al., "A new technique for establishing dry weight in hemodialysis patients via whole body bioimpedance," Kidney Int., 2002, 61:2250-2258.

Chamney et al., "A whole-body model to distinguish excess fluid from the hydration of major body tissues," Am J Clin Nutr, 2007, 85:80-89.

Kuhlmann et al., "Bioimpedance, dry weight and blood pressure control: new methods and consequences," Current Opinion in Nephrology and Hypertension, 2005, 14:543-549.

Piccoli et al., "A new method for monitoring body fluid variation by bioimpedance analysis: The RXc graph," Kidney Int., 1994, 46:534-539.

Zhu et al., "Adjustment of dry weight in hemodialysis patients using intradialytic continuous multifrequency bioimpedance of the calf," Int J Artif Organs, 2004, 27:104-109.

Zhu et al., "A method for the estimation of hydration state during hemodialysis using a calf bioimpedance technique," Physiol Meas, 2008, 29:S503-S516.

Zhu et al., "Prediction of Normal Hydration State in Hemodialysis Patients Using Calf Resistivity" [Abstract], J Am Soc Nephrol, 2010, 21:435A.

Supplementary European Search Report for EP Application No. EP11833309.5, dated Oct. 30, 2017, 9 pages.

Zhu, F., et al., "Continuous Measurement of Calf Resistivity in Hemodialysis Patients using Bioimpedance Analysis," 2006 International Conference of the IEEE Engineering in Medicine and Biology Society, New York, NY, 2006, pp. 5126-5128.

International Search Report and Written Opinion for International application No. PCT/US2011/055916, dated May 2, 2012, 11 pages.

* cited by examiner

DRY WEIGHT PREDICTOR

CROSS-REFERENCE TO RELATED CASE FOR U.S. NATIONAL PHASE APPLICATION

This application claims the benefit under 35 USC § 119(e) of U.S. Provisional Application No. 61/393,544 filed Oct. 15, 2010, the contents of which in its entirety is hereby incorporated by reference.

FIELD

This disclosure relates to the prediction/estimation of the dry weight of an individual. Although of general value, knowledge of an individual's dry weight is especially important for renal patients undergoing dialysis procedures.

BACKGROUND

Hydration status is an important issue in long-term dialysis patients and is related to clinical outcome. Chronic overhydration is associated with left ventricular hypertrophy, left ventricular dilatation, arterial hypertension, and eventually the development of congestive heart failure. High intradialytic weight gain on top of chronic overhydration further increases the burden for the cardiovascular system. Management of hydration status involves restriction of sodium intake and, to the extent possible and over time, attainment of a post-dialysis weight equal to the patient's dry weight.

Dry weight may be defined as the weight at which an individual is as close as possible to a normal hydration state without experiencing symptoms indicative of over or underhydration. Clinically, dry weight is determined as the lowest weight a patient can tolerate without developing intra or interdialytic symptoms. This clinical assessment is hampered by the fact that some liters of fluid may accumulate in the body before edema becomes clinically evident and that it does not account for changes in lean body mass, fat mass or nutritional status over time. In addition, some patients may have symptoms on dialysis because of cardiac disease or a higher ultrafiltration rate while still being overhydrated.

Various approaches towards a more objective measure of dry weight have been developed, such as blood volume monitoring, ultrasound assessment of inferior vena cava diameter, and several biochemical parameters, such as brain or atrial natriuretic peptide. None of these measures, however, gives an accurate estimate of dry weight. Consequently, a majority of dialysis patients may be overhydrated, particularly because this is associated with asymptomatic dialysis.

Efforts have been made in the past to use bioimpedance technology to facilitate the dry weight prescription process. See, for example, Kuhlmann et al., "Bioimpedance, dry weight and blood pressure control: new methods and consequences," *Current Opinion in Nephrology and Hypertension*, 2005, 14:543-549. Three different bioimpedance approaches to determine dry weight have been published. The normovolemichypervolemic slope method (see, for example, Chamney et al., "A new technique for establishing dry weight in hemodialysis patients via whole body bioimpedance," *Kidney Int*, 2002, 61:2250-2258) applies whole body multi-frequency bioimpedance to assess predialysis total body extracellular fluid volume and compares the extracellular fluid volume/body weight relation at hypervolemia with the standard value in normovolemic individuals. The resistance-reactance graph method (see, for example, Piccoli et al., "A new method for monitoring body fluid variation by bioimpedance analysis," *Kidney Int*, 1994:534-539) uses whole body single frequency bioimpedance at 50 kHz for assessment of hydration state and nutritional status from height-adjusted resistance and reactance. The resulting resistance-reactance vector is set in relation to a distribution range in a normovolemic population. An alternative method (see, for example, Zhu et al., "Adjustment of dry weight in hemodialysis patients using intradialytic continuous multifrequency bioimpedance of the calf," *Int J Artif Organs*, 2004, 12:104-109, and Zhu et al., "A method for the estimation of hydration state during hemodialysis using a calf bioimpedance technique," *Physiol Meas*, 2008:S503-S516) uses segmental bioimpedance in the form of continuous intradialytic calf bioimpedance to record changes in calf extracellular volume during dialysis. Dry weight by this method is defined as the weight at which calf extracellular volume is not further reduced without hypotension symptoms with ongoing ultrafiltration.

None of these bioimpedance methods has gained much popularity. Part of the problem has been the lack of an established "gold standard" for dry weight determination. In addition, intradialytic methods impose added cost and complexity to the dialysis procedure, which is already expensive and time consuming.

Accordingly, there exists a need for improved methods for predicting dry weight and, in particular, improved bioimpedance methods which are easy to use and generate reliable dry weight predictions/estimations. The present disclosure is addressed to this long standing problem in the art.

SUMMARY

In accordance with a first aspect, a method is disclosed for predicting/estimating an individual's dry weight which includes:

(a) obtaining a measured value indicative of the extracellular fluid volume of the individual's calf (101) using a bioimpedance measurement technique (303);

(b) obtaining a measured value (309) indicative of the circumferential size C of the individual's calf (101);

(c) determining (301) a normalized value indicative of the extracellular fluid volume of the individual's calf (101) from the measured values of steps (a) and (b) and the individual's body mass index (BMI) value;

(d) determining (301) a difference value between the normalized value of step (c) and a reference value for the normalized value; and (e) using (301) the difference value of step (d) to determine a predicted/estimated value for the individual's dry weight.

In accordance with a second aspect, a method is disclosed for establishing a target dry weight for an individual which includes:

(a) obtaining a measured resistance value R indicative of the extracellular fluid volume of the individual's calf (101) using a bioimpedance measurement technique (303);

(b) obtaining a measured value (309) indicative of the circumferential size C of the individual's calf (101);

(c) determining (301) a normalized resistivity value $\rho_N$ indicative of the extracellular fluid volume of the individual's calf (101) from the measured values of steps (a) and (b), the individual's BMI value, and an equation of the form:

$$\rho_N = R \cdot C^2/(4\pi L \cdot \text{BMI});$$

(d) determining (301) a difference value ΔnRho between the normalized value $\rho_N$ of step (c) and a reference value K for the normalized value using an equation of the form:

$$\Delta nRho = -(\rho_N - K); \text{ and}$$

(e) using (301) the difference value of step (d) to determine the target dry weight;

wherein the target dry weight TDW satisfies the equation:

$$WT - (\alpha \cdot \Delta nRho + \beta) - 1.0 \leq TDW \leq WT - (\alpha \cdot \Delta nRho + \beta) + 1.0$$

where the equation is in kilograms, WT is the individual's weight at the time steps (a) and (b) are performed, and $\alpha$ and $\beta$ are predetermined constants.

In accordance with a third aspect, a method is disclosed for establishing a target dry weight for an individual which includes:

(a) obtaining a measured resistance value R indicative of the extracellular fluid volume of the individual's calf (101) using a bioimpedance measurement technique (303);

(b) obtaining a measured value (309) indicative of the circumferential size C of the individual's calf (101);

(c) determining (301) a normalized resistivity value $\rho_N$ indicative of the extracellular fluid volume of the individual's calf (101) from the measured values of steps (a) and (b), the individual's BMI value, and an equation of the form:

$$\rho_N = R \cdot C^2 / (4\pi L \cdot BMI);$$

(d) determining (301) a difference value ΔnRho between the normalized value $\rho_N$ of step (c) and a reference value K for the normalized value using an equation of the form:

$$\Delta nRho = -(\rho_N - K); \text{ and}$$

(e) using (301) the difference value of step (d) to determine the target dry weight;

wherein the target dry weight TDW satisfies the equation:

$$WT - \lambda \cdot \exp[(100 \cdot \Delta nRho/(\text{ohm-meter}^3/\text{kilogram}))^\xi] - 1.0 \leq TDW \leq WT - \lambda \cdot \exp[(100 \cdot \Delta nRho/(\text{ohm-meter}^3/\text{kilogram}))^\xi] + 1.0$$

where the equation is in kilograms, WT is the individual's weight at the time steps (a) and (b) are performed, $\rho_N$ and K are in ohm-meter$^3$/kilogram, and $\lambda$, and $\xi$ are constants.

In accordance with a fourth aspect, a method for reducing the fluid overload of an individual is disclosed which includes;

(a) obtaining a measured value indicative of the extracellular fluid volume of the individual's calf (101) using a bioimpedance measurement technique;

(b) obtaining a measured value (309) indicative of the circumferential size C of the individual's calf (101);

(c) determining (301) a normalized value indicative of the extracellular fluid volume of the individual's calf (101) from the measured values of steps (a) and (b) and the individual's BMI value;

(d) determining (301) a difference value between the normalized value of step (c) and a reference value for the normalized value;

(e) using (301) the difference value of step (d) to determine a predicted/estimated value for the individual's dry weight; and (f) reducing the fluid overload of the individual based at least in part on the predicted/estimated dry weight.

In accordance with a fifth aspect, a medicament is disclosed for use in a method for reducing the fluid overload of an individual, the method including the following steps:

(a) obtaining a measured value indicative of the extracellular fluid volume of the individual's calf (101) using a bioimpedance measurement technique (303);

(b) obtaining a measured value (309) indicative of the circumferential size C of the individual's calf (101);

(c) determining (301) a normalized value indicative of the extracellular fluid volume of the individual's calf (101) from the measured values of steps (a) and (b) and the individual's BMI value;

(d) determining (301) a difference value between the normalized value of step (c) and a reference value for the normalized value;

(e) using (301) the difference value of step (d) to determine a predicted/estimated value for the individual's dry weight; and (0 reducing the fluid overload of the individual by determining the dosage and/or the administration scheme of the medicament at least in part based on the predicted/estimated dry weight.

Apparatus (e.g., 1-7, 103, 105, and 301-311) for practicing the above methods is also disclosed.

The reference numbers used in the above summaries of the various aspects of the disclosure are only for the convenience of the reader and are not intended to and should not be interpreted as limiting the scope of the invention. More generally, it is to be understood that both the foregoing general description and the following detailed description are merely exemplary of the invention and are intended to provide an overview or framework for understanding the nature and character of the invention.

Additional features and advantages of the invention are set forth in the detailed description which follows, and in part will be readily apparent to those skilled in the art from that description or recognized by practicing the invention as exemplified by the description herein. The accompanying drawings are included to provide a further understanding of the invention, and are incorporated in and constitute a part of this specification. It is to be understood that the various features of the invention disclosed in this specification and in the drawings can be used in any and all combinations.

Figure 1:
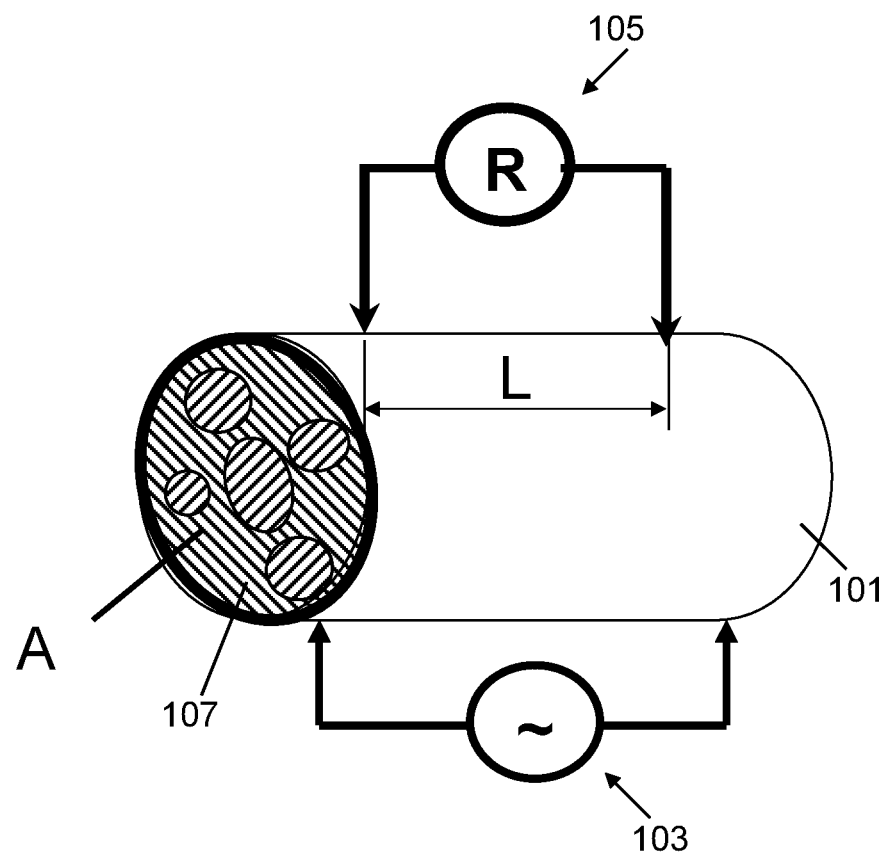
FIG. 1 is a schematic drawing illustrating the elements of a bioimpedance measurement.

The reference numbers used in the figures refer to the following:

1 stimulating electrode
2 recording electrode
3 pressure cuff
4 recording electrode
5 stimulating electrode
7 tension sensor
51 nRho curve
53 R(t=0)/R(t) curve
55 three hour line
57 flattening of R(t=0)/R(t) curve
101 individual's calf
103 bioimpedance stimulating system
105 bioimpedance recording system
107 cross-section of calf
151 Eq. (7b) curve
153 Eq. (7a) curve
155 Eq. (10) curve
301 CPU
303 bioimpedance system
305 input module
307 display module
309 circumference measuring module
311 tension testing module

DETAILED DESCRIPTION

As discussed above, the present disclosure relates to the problem of predicting/estimating the dry weight of an individual. The individual will typically be a patient undergoing hemodialysis or peritoneal dialysis as a result of renal failure, it being understood that the procedures and apparatus disclosed herein can also be used to assess the hydration state of patients suffering from diseases other than renal failure (acute kidney disease), e.g., cardiac failure, liver failure, malnutrition, venous thrombosis, and/or chronic kidney disease which has not yet led to the need for dialysis treatment. Particularly, knowledge of dry weight can be of value with cardiac failure patients who are being treated with diuretics to reduce their fluid volume. As in dialysis, knowledge of the patient's dry weight is of clinical significance in deciding how much diuretic to prescribe.

In addition, the procedures and apparatus can be used in connection with estimating the hydration state of normal subjects, e.g., individuals (athletes) participating in strenuous activity under high temperature and/or high humidity conditions. More generally, knowledge of an individual's dry weight may be beneficial in terms of controlling the intake of minerals, particularly sodium-containing minerals, in the individual's diet, e.g., the individual (either a patient or a normal subject) can monitor his or her water retention as a result of sodium intake by comparing his or her weight to an estimated dry weight determined in accordance with the present disclosure. Having information regarding dry weight may be of particular interest to fitness enthusiasts and other persons particularly concerned with their state of health. Whether a patient or a normal subject, the procedures and apparatus disclose herein will typically be employed at various points in time so that the predicted/estimated dry weight will be current with changes in the individual's body composition, e.g., changes in the individual's fat and/or muscle content as a result of diet and/or exercise or the lack thereof.

The dry weight determination (dry weight estimation or prediction) disclosed herein is based on the performance of a bioimpedance measurement on the individual's calf. The purpose of the measurement is to obtain information concerning the calf's extracellular volume (ECV) since as discussed fully below, in accordance with the present disclosure, it has been found that by normalizing such a measured value using the individual's body mass index (BMI) and then determining the difference between the normalized value and a constant (e.g., a constant determined for a relevant population of normal subjects, such as the mean minus one standard deviation of the normalized bioimpedance value for the population), a high correlation is achieved between predicted/estimated dry weight and actual dry weight determined using a gold standard.

FIG. 1 is a schematic diagram illustrating the basic elements involved in the performance of a bioimpedance measurement on an individual's calf 101. As shown, the bioimpedance system includes a stimulating system 103 which applies an AC current at two spaced apart locations on the surface of the individual's calf and a recording system 105 which detects the resulting AC voltage difference at two spaced apart locations, which are typically (preferably) inboard of the stimulating locations. The AC voltage difference is then used to calculate a bioimpedance value or, in some cases, simply a resistance (R) value. The procedure can be performed at one frequency, e.g., 5 kilohertz, or at a plurality of frequencies in which case the technique is often referred to as bioimpedance spectroscopy (BIS).

Figure 2:
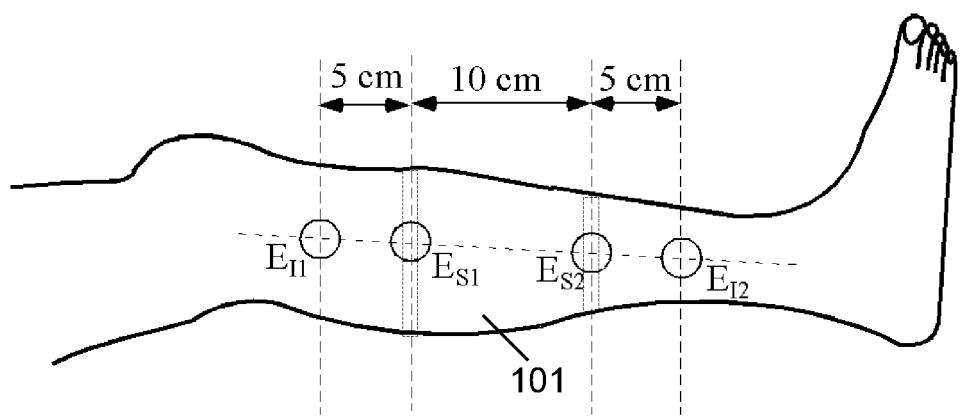
FIG. 2 is a schematic drawing illustrating a representative placement of electrodes on an individual's calf for performance of a bioimpedance measurement for the calf.
Figure 3:
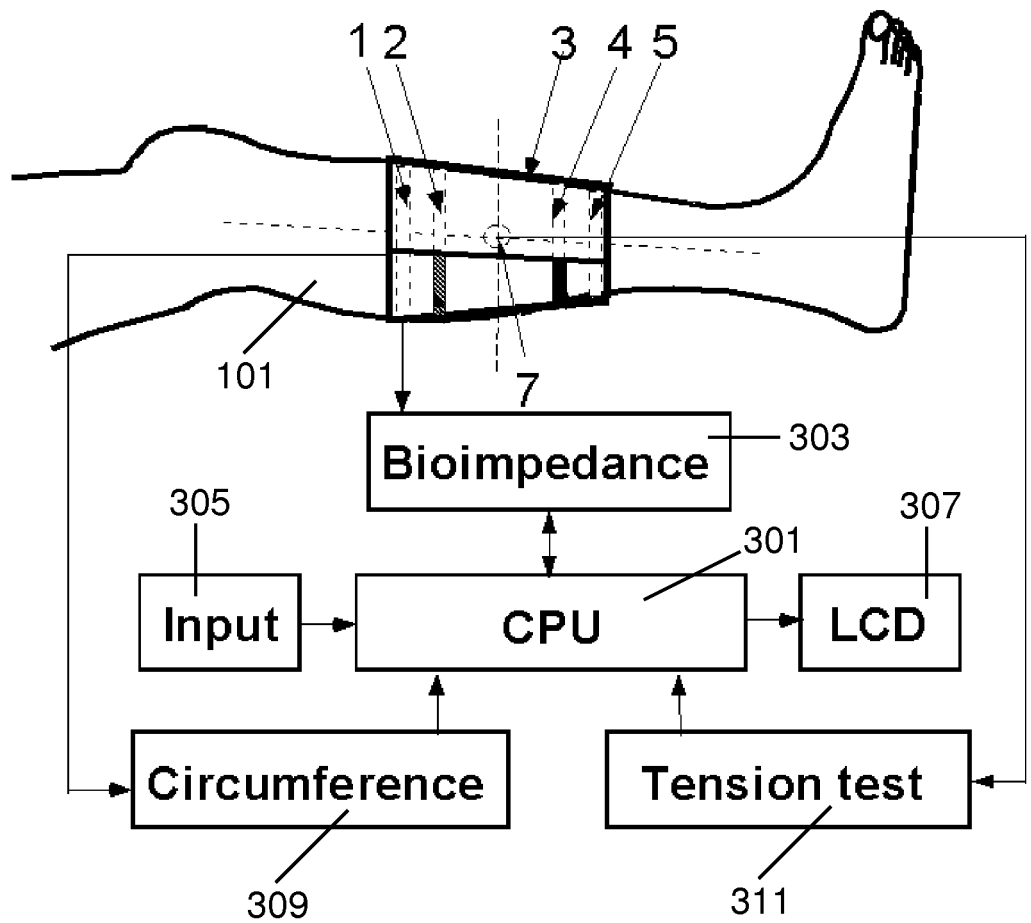
FIG. 3 is a schematic drawing illustrating representative hardware and software components for practicing the dry weight prediction/estimation techniques disclosed herein.

FIG. 2 shows representative locations on an individual's calf of the stimulating ($E_{I1}$ and $E_{I2}$) and recording ($E_{S1}$ and $E_{S2}$) electrodes used in the bioimpedance procedure. As illustrated in this figure, a convenient location for $E_{S1}$ is at the calf's maximal circumference, with $E_{S2}$ being placed 10 centimeters below $E_{S1}$, and $E_{I1}$ and $E_{I2}$ being placed 5 centimeters above and below $E_{S1}$ and $E_{S2}$, respectively. FIG. 3 illustrates a representative processing system for receiving and analyzing bioimpedance and other data for the individual whose dry weight is to be predicted/estimated. As shown in this figure, the system can include a central processing unit (CPU) 301, which receives measured data from bioimpedance system 303, as well as other types of input from input module 305, e.g., input relating to the individual's sex, weight, height, etc., which can be keyed in or electronically provided. The system can also include a display module 307, in particular a display module employing a liquid crystal display (LCD), for providing information to the user as well as a keyboard (not shown) connected to input module 305 with which the user can provide information to the system.

As illustrated in FIG. 3, bioimpedance system 303 can employ a pressure cuff 3 which carries stimulating electrodes 1,5 (e.g., $E_{I1}$ and $E_{I2}$ of FIG. 2) and recording electrodes 2,4 (e.g., $E_{S1}$ and $E_{S2}$ of FIG. 2). The electrodes can be disposable or reusable as desired. The pressure cuff can be employed as part of the process of determining a value for the circumference of the patient's calf, e.g., through the use of circumference module 309. In one embodiment, using tension sensor 7, a tension test can be performed by tension testing module 311 to determine that the individual's calf has been compressed to a desired extent before the circumference is determined. The circumference can be determined by various methods such as by an electrical resistance technique of the type disclosed in PCT Patent Publication No. WO 2005/027717, the contents of which in their entirety are incorporated by reference. Particularly, the circumference can be measured at the locations of electrodes 2 and 4 (or at one or more other convenient locations) and, if multiple measurements are made, averaged to provide a mean value. Rather than using a pressure cuff, the circumference can be determined manually using a flexible tape measure. Again, one measurement can be used, or multiple measurements can be made and then averaged. Other techniques for determining the circumference of the individual's calf can be used as desired. However determined, a circumference value is ultimately provided to CPU 301 and then used in determining a resistivity value for the individual's calf.

The resistivity value is determined from the equation:

$$\rho = R \cdot A/L = R \cdot C^2/(4\pi L) \quad \text{Eq. (1)}$$

where, as illustrated in FIG. 1, L is the spacing between the recording electrodes used in the bioimpedance procedure, A is the area of a representative cross-section 107 of the individual's calf, C is the circumference value for the individual's calf obtained from one or more circumference measurements performed on the calf, and R is the resistance value for the calf obtained from the bioimpedance procedure. In practice, it has been found that resistance values obtained for a stimulating frequency of 5 kilohertz results in highly accurate predictions/estimations of dry weight, it being understood that other frequencies can be used and that instead of a resistance value, a value for the magnitude of the impedance (|Z|) at 5 kilohertz or at another frequency can be used. In a similar manner, combinations of resistance values and/or impedance values at a plurality of frequencies can be used, e.g., an average R value, an average |Z| value, or an average over R and |Z| values for a plurality of frequencies (e.g., 1, 5, and 10 kilohertz) can be used if desired. Other variations on the particular output from the bioimpedance procedure used in the predictive process will be evident to persons skilled in the art from the present disclosure. For ease of presentation, it the following discussion, it will be assumed that a resistance value at 5 kilohertz has been chosen as the bioimpedance value.

The $\rho$ value obtained from Eq. (1) is next normalized by being divided by the individual's body mass index (BMI), i.e., the normalized resistivity $\rho_N$ (also referred to herein as "nRho") is given by:

$$\rho_N = \rho/BMI \quad \text{Eq. (2)}$$

where the individual's BMI is his/her mass in kilograms divided by his/her height in meters squared.

The normalized resistivity value is then offset by a reference value for the normalized resistivity value to produce a new variable ΔnRho, which as demonstrated below, has been found to be highly effective in predicting/estimating dry weight. Specifically, ΔnRho is given by:

$$\Delta nRho = -(\rho_N - K) \quad \text{Eq. (3)}$$

where K is the reference value (also referred to herein as the "offset constant" or simply the "K value").

The value of the offset constant can be determined in various ways. One way that has been found to work effectively is to base the constant on a normalized resistivity value which is representative of a population of reference individuals (e.g., normal subjects, particularly, healthy subjects) of which the individual for whom a dry weight value is desired is a member. For example, for a male individual, the population can be normal males, and for a female individual, the population can be normal females. The normalized resistivity value representative of the population can then be a mean normalized resistivity value measured for a representative sample of the population. To minimize the possibility that the predicted/estimated dry weight is too low, in practice it has been found helpful to subtract one standard deviation from the mean value and use that value as the offset constant. Because normalized resistivity increases as extracellular volume decreases, the subtraction of one standard deviation means that the individual's $\rho_N$ value is compared to the more hydrated end of normal in computing ΔnRho.

The population used in determining the K value can be more specific than merely males/females. Particularly, the population can be for males/females of a particular age, race, and/or ethnicity. Likewise, the population can vary with geographical location. Physical characteristics can also be relied on in determining the value of K to use in calculating ΔnRho. For example, it has been found that for highly obese males, better dry weight predictions/estimations are achieved by using a K value of $18.8 \times 10^{-2}$ ohm-meter$^3$/kilogram, as opposed to the value $18.5 \times 10^{-2}$ ohm-meter$^3$/kilogram, which works successfully with non-highly obese individuals. For females, the corresponding values are $16.4 \times 10^{-2}$ ohm-meter$^3$/kilogram for highly obese females and $19.4 \times 10^{-2}$ ohm-meter$^3$/kilogram for non-highly obese females. Accordingly, in certain embodiments, it may be helpful to have a lookup table (e.g., a lookup multi-dimensional matrix) and/or a look-up function or set of functions which provide an appropriate K value based on the individual's age, sex, race, ethnicity, obesity level, etc. and/or combinations thereof.

As indicated above, a central aspect of the present disclosure is the discovery that ΔnRho is a highly effective variable in predicting/estimating dry weight. In particular, it has been found that the difference in weight (ΔWT) between an individual's weight (WT) at the time ΔnRho is measured and the individual's dry weight (DW) is a function of ΔnRho:

$$\Delta WT = f(\Delta nRho) \quad \text{Eq. (4)}$$

where $$\Delta WT = WT - DW. \quad \text{Eq. (5)}$$

Moreover, the function f(ΔnRho) can, in many cases, be a simple linear dependence, i.e., ΔWT can be written as:

$$\Delta WT = \alpha \cdot \Delta nRho + \beta, \quad \text{Eq. (6a)}$$

where α and β are constants.

Substituting Eq. (6a) in Eq. (5) and rearranging then gives:

$$DW=WT-(\alpha \cdot \Delta nRho+\beta).\qquad\text{Eq. (7a)}$$

As discussed below, in an initial application of the present disclosure, $\alpha$ and $\beta$ values of $0.5\times10^2$ kilogram$^2$/ohm-meter$^3$ and 0.84 kilograms, respectively, were determined for a population of 27 patients. For a nine-member subset of this population, $\alpha$ and $\beta$ values of $0.2\times10^2$ kilogram$^2$/ohm-meter$^3$ and 0.4 kilograms, respectively, were determined. In each case, the values were obtained using a fitting procedure in which Eq. (7a) was fitted to dry weight data obtained using a "gold standard" technique (also referred to herein as a "gold standard approach") for estimating/predicting dry weight (see below). These particular values are, of course, merely representative values for the $\alpha$ and $\beta$ parameters, the specific values used in any particular application of the present disclosure depending on the one or more populations of normal subjects used in determining the one or more K values and the gold standard technique used in the fitting procedure, as well as the size of the population used to determine the $\alpha$ and $\beta$ parameters, larger populations generally producing more reliable values. Moreover, if desired, Eq. (7a) can be modified to include additional terms and fitting parameters for specific applications. The values of $\alpha$ and $\beta$ can be expected to be different for such a modified equation. More generally, instead of a simple linear function, the function f($\Delta$nRho) can be more complex, in particular a second order polynomial, with more/different fitting coefficients. However, no matter what its particular form, in accordance with the teachings herein, the formula for predicting/estimating dry weight will at least in part be a function of $\Delta$nRho.

In particular, in one embodiment, f($\Delta$nRho) can be of the following form:

$$\Delta WT=f(\Delta nRho)=\lambda\cdot\exp[(100\cdot\Delta nRho/(\text{ohm-meter}^3/\text{kilogram}))^\xi]\qquad\text{Eq. (6b)}$$

so that DW is of the form:

$$DW=WT-\lambda\cdot\exp[(100\cdot\Delta nRho/(\text{ohm-meter}^3/\text{kilogram}))^\xi]\qquad\text{Eq. (7b)}$$

where $\lambda$ and $\xi$ are constants and, as above, $\Delta$nRho is measured in ohm-meter$^3$/kilogram.

For the nine-member population referred to above, $\lambda$ and $\xi$ values of $0.4\times10^2$ kilograms$^2$/ohm-meter$^3$ and ⅓, respectively, were determined using the same gold standard as that used to determine the $\alpha$ and $\beta$ parameters. As with the $\alpha$ and $\beta$ parameters, the particular values for the $\lambda$ and $\xi$ parameters will depend on the populations used in determining the values, including the size of those populations. Also, if desired, Eq. (7b) can be modified to include additional terms and fitting parameters for specific applications. For ease of presentation, Eqs. (7a) and 7(b) will be referred to hereinafter as Eq. (7) when discussing features of the present disclosure applicable to both equations.

In some cases, prescribing physicians may use a dry weight prediction/estimation based on $\Delta$nRho, e.g., a prediction/estimation based on Eq. (7), as a starting point for setting a target weight for a dialysis session, as opposed to the ultimate prescribed value. In one embodiment, the physician may set a higher/lower target weight than predicted/estimated by Eq. (7) because of the susceptibility/lack of susceptibility of the patient to clinical symptoms associated with excessive fluid removal. Typically, however, the target dry weight will be within ±1 kilogram of that predicted/estimated using a $\Delta$nRho analysis and in many cases within ±0.5 kilograms. In one embodiment, the prescribed target weight (TDW) can satisfy the equation:

$$WT-\Delta WT-1.0\leq TDW\leq WT-\Delta WT+1.0\qquad\text{Eq. (8)}$$

or, in many cases, the equation:

$$WT-\Delta WT-0.5\leq TDW\leq WT-\Delta WT+0.5,\qquad\text{Eq. (9)}$$

where, as defined above, WT is the individual's weight at the time $\Delta$nRho is measured and $\Delta WT=f(\Delta nRho)$ is given by Eq. 6(a) or Eq. 6(b). As will be evident, Eqs. (8) and (9) are in kilograms.

Figure 4:
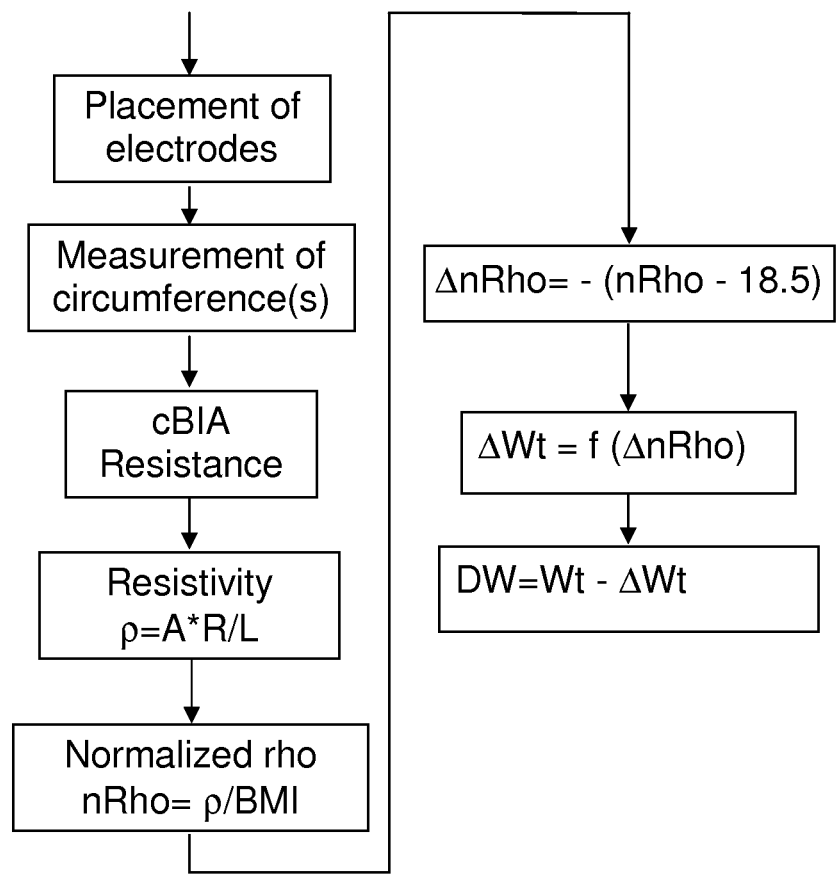
FIG. 4 is a flow chart illustrating an embodiment of the dry weight prediction/estimation techniques disclosed herein.

FIG. 4 sets forth in flow chart form the above steps of the procedure, beginning with the placement of the electrodes and ending with a calculation of a predicted/estimated dry weight value. The 18.5 value used in this figure is for a male patient, the corresponding value for a female patient being 19.4. In the case of obese patients, the numbers are 18.8 and 16.4 for males and females, respectively. In terms of clinical practice, an estimated time for performing these steps is on the order of five minutes, thus making the procedure entirely practical for routine use. Particularly for a dialysis patient, a dry weight prediction/estimation can easily be obtained just prior to a dialysis session, just after a session (a preferred time), and/or at any time between sessions and used by the prescribing physician to establish the amount of fluid to be removed from the patient during the next session. In one embodiment, dry weight predictions/estimations can also be obtained during a dialysis session. Whenever taken, the dry weight predictions/estimations can be charted over time to track changes in the individual's body makeup as a result of, for example, changes in diet and/or activity levels.

We turn now to a discussion of the gold standard technique used to determine the $\alpha$ and $\beta$ values for Eq. (7a) set forth above. We then show the predictive power of the procedures of the present disclosure and finally conclude the discussion of Eq. (7a) with a comparison between the calf bioimpedance procedures disclosed herein and a prior technique based on whole body bioimpedance. Following those discussions, we turn to Eq. (7b) and illustrate its ability to predict/estimate dry weight for patients undergoing dialysis.

Figure 5:
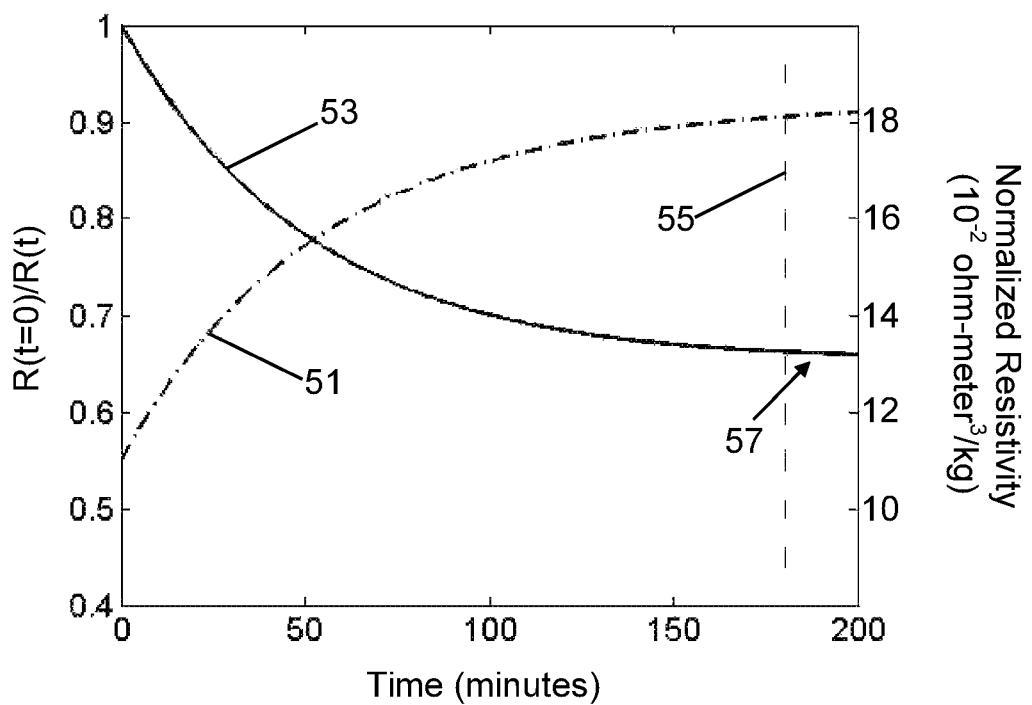
FIG. 5 is a plot showing normalized resistivity (curve 51) and R(t=0)/R(t) (curve 53) versus time for the gold standard technique which was used to demonstrate the effectiveness of the dry weight prediction/estimation techniques disclosed herein.
Figure 6:
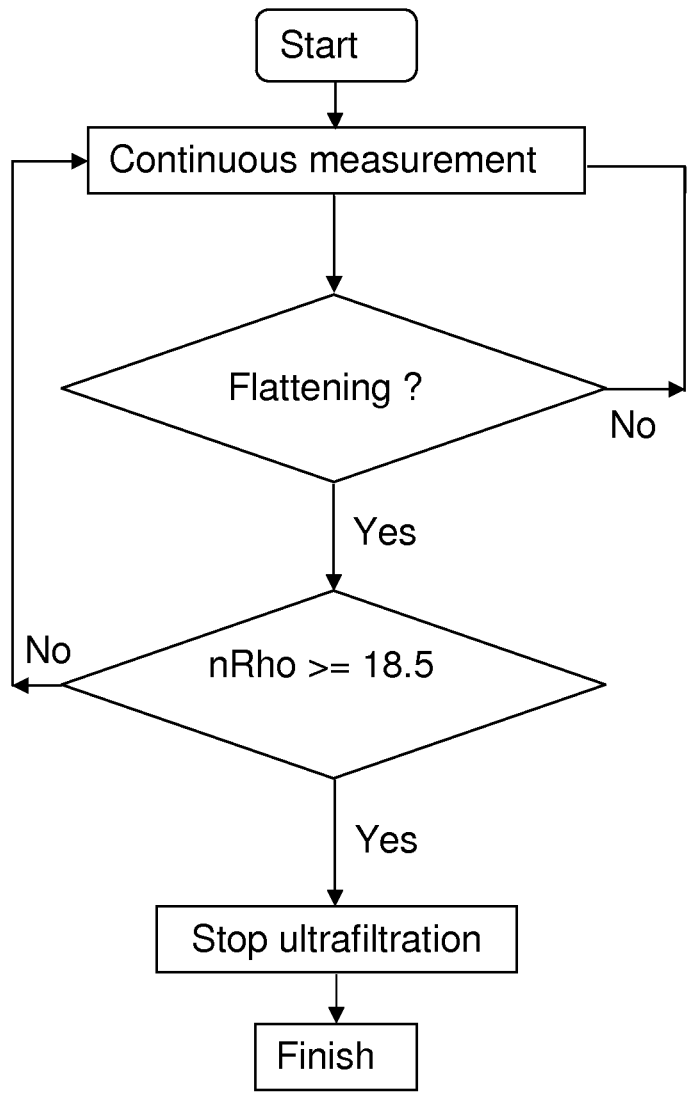
FIG. 6 is a flow chart illustrating the steps of the gold standard technique.
Figure 8:
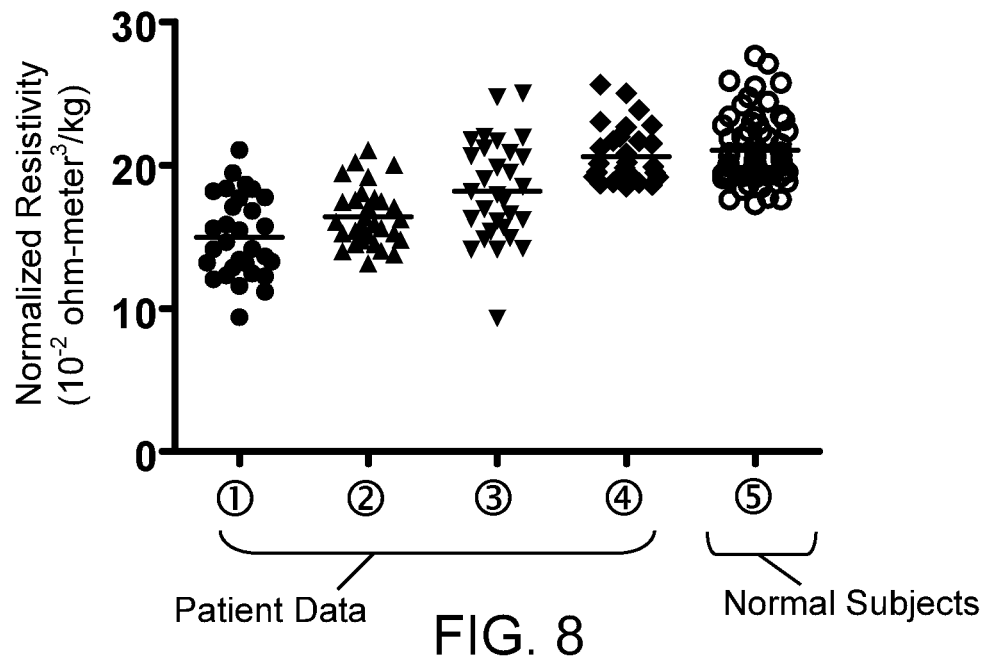
FIG. 8 is a plot demonstrating the effectiveness of the gold standard technique in predicting/estimating dry weight values.
Figure 9:
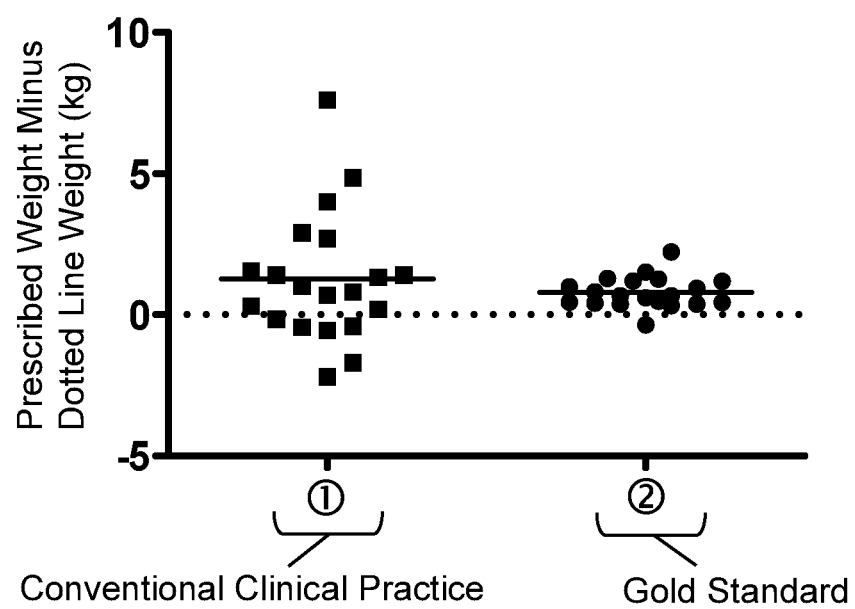
FIG. 9 is a further plot demonstrating the effectiveness of the gold standard technique in predicting/estimating dry weight values.

The gold standard technique for dry weight prediction/estimation used herein was based on dry weight determinations obtained for a population of hemodialysis patients by performing continuous calf bioimpedance spectroscopy (cBIS) measurements on the patients as they were undergoing treatment. Dry weight values were determined (estimated) using a combination of (1) flattening of the calf extracellular resistance curve and (2) an increase in normalized resistivity $\rho_N$ to a value indicative of the hydration state of normal subjects (Zhu et al., Physiol Meas 2008). FIGS. 5 and 6 illustrate the procedure used, FIG. 7 shows the experimental protocol for a representative patient, and FIGS. 8 and 9 show the results obtained.

FIG. 5 is a representative plot for a male patient whose course of treatment has brought him to a point where at the end of a dialysis session, the patient's weight is at his dry weight, the desired end point. Specifically, curve 51 is a plot of normalized resistivity $\rho_N$ in $10^{-2}$ ohm-meter$^3$/kilogram (right hand vertical axis) versus time in minutes (horizontal axis), while curve 53 is a plot of the function R(t=0)/R(t) (left hand vertical axis) versus time, where R is the measured calf bioimpedance resistance at 5 kilohertz. Vertical line 55 marks three hours, the normal duration of a dialysis session. As can be seen in this figure, the R(t=0)/R(t) curve (curve 53) drops rapidly at the beginning of the session and then becomes essentially flat (see reference number 57), while the normalized resistivity increases with time, eventually reaching a value of 18.5×10$^{-2}$ ohm-meter$^3$/kilogram, which was taken as normal hydration for male patients in these experiments.

FIG. 6 shows in flow chart form the strategy used in these experiments to determine gold standard dry weight values. As shown in this figure, a combination of flattening and a normalized resistivity value (nRho value) greater than or equal to 18.5×10$^{-2}$ ohm-meter$^3$/kilogram was taken as indicative of a male patient having reached his dry weight, and thus the dialysis procedure was stopped at this point and the patient's weight (the dry weight) was recorded. Flattening was defined as in Zhu et al., *Physiol Meas, supra*, the contents of which in their entirety are incorporated herein by reference. For female patients, 19.4×10$^{-2}$ ohm-meter$^3$/kilogram was used as the standard for the patient having reached her dry weight, instead of 18.5×10$^{-2}$ ohm-meter$^3$/kilogram in the procedure of FIG. 6 and the plot of FIG. 5.

Figure 7:
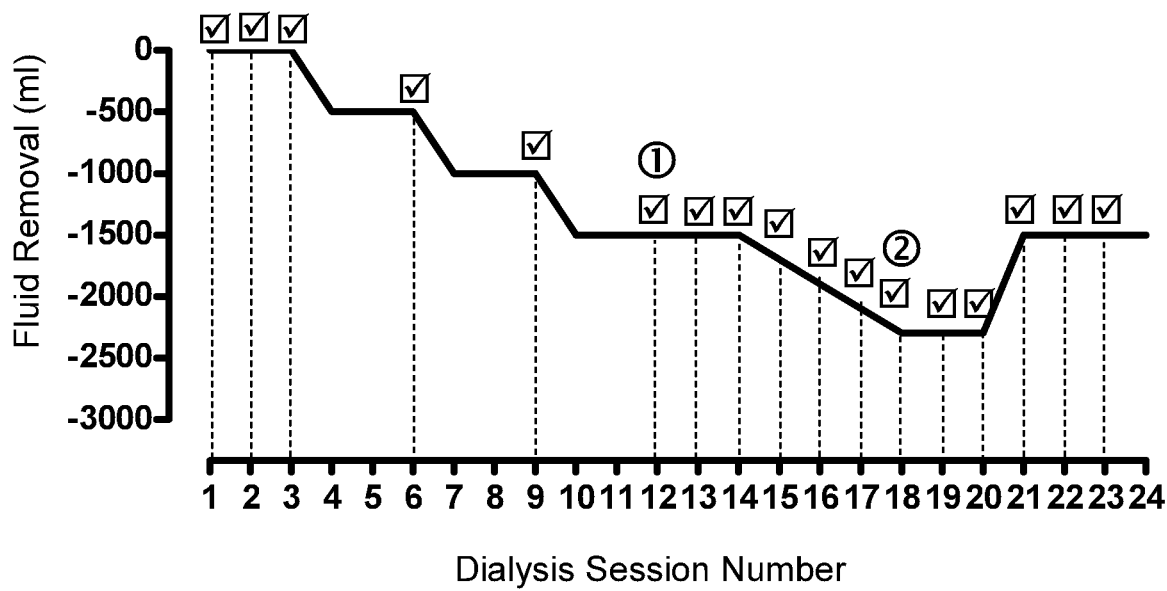
FIG. 7 is a schematic diagram illustrating an experimental protocol used in the gold standard technique.

FIG. 7 shows a full experimental protocol (e.g., 24 dialysis sessions) for a typical patient. The vertical axis shows the amount of fluid in milliliters removed from the patient during each session. For a population of twenty patients, the average weight of a patient at the beginning of the study (the baseline average post-dialysis weight) was 78.3 kilograms, while at the end of the dialysis sessions, it was 77.1 kilograms (the final average post-dialysis weight, i.e., the average dry weight). The check marks show sessions for which calf bioimpedance measurements were made. The session marked with the circled-1 symbol was the first session at which flattening and a $\rho_N$ value indicative of the patient having achieved dry weight (e.g., 18.5×10$^{-2}$ ohm-meter$^3$/kilogram for a male patient and 19.4×10$^{-2}$ ohm-meter$^3$/kilogram for a female patient) were observed. Accordingly, for this representative patient, the patient's weight at session 12 would be taken as the gold standard dry weight. The course of treatment for the various members of the study was not identical, but the protocol of FIG. 7 is representative.

FIG. 8 shows the effectiveness of the above gold standard technique in bringing patients to their dry weight. In this figure, the vertical axis shows normalized resistivity in 10$^{-2}$ ohm-meter$^3$/kilogram, while the first and third columns show the normalized resistivity values of the patients pre-dialysis and post-dialysis at the beginning of the experiment (e.g., at session 6 for the representative patient of FIG. 7) and the second and fourth columns show the normalized resistivity values pre- and post-dialysis after the patients had been in the course of treatment for a sufficient period of time so that they reached dry weight at the end of the dialysis session (e.g., session 12 for the representative patient of FIG. 7). The fifth column shows normalized resistivity values for normal subjects. In each column, the horizontal line shows the mean value of the normalized resistivity, which was 14.99±0.52 for the first column and 21.04±0.3 for the fifth column. (For normal males having BMI values less than 30, the mean of nRho is 19.6±2.3×10$^{-2}$ ohm-meter$^3$/kilogram, while for females it is 20.9±2.7×10$^{-2}$.) As can be seen in this figure, the gold standard approach for defining dry weight used herein increased the patient's normalized resistivity both pre- and post-dialysis and ultimately brought the post-dialysis value up to a value substantially equal to that of normal subjects.

As further validation of the gold standard approach, after the dry weight value had been reached (e.g., dialysis session 12 in FIG. 7), the experiment was continued (IRB approved) with the amount of fluid removed per session being slowly increased until the patient showed clinical signs indicative of the removal of too much fluid (e.g., cramps, headache, hypotension). For the representative patient of FIG. 7, the session marked with a circled-2 symbol constitutes the first such session. A gold standard for dry weight should come close to this level without reaching it. FIG. 9 illustrates that this fine line between enough, but not too much, fluid removal per dialysis session is achieved by the combination of flattening and normalized resistivity equaling that of normal subjects.

In particular, FIG. 9 compares prescribed target weights (dry weights) for dialysis sessions where the prescribed weight was based on conventional clinical practices (first column) and where it was based on the above gold standard for dry weight (second column). The horizontal dotted line marks the level at which too much fluid was removed, and the vertical axis shows the difference in kilograms between the prescribed weight and the dotted line. Ideally, the prescribed weight should be as close as possible to the dotted line without going under it. As can be seen in FIG. 9, the gold standard approach used herein achieves this goal, while the prescriptions based on conventional clinical practice show substantial scatter, with many prescriptions being below the dotted line or substantially above it. Quantitatively, the average difference between the prescribed weight and the dotted line was 1.39±2.18 kilograms using the clinical approach, while it was only 0.75±0.55 kilograms using the gold standard approach.

Although, as the data of FIGS. 8 and 9 demonstrates, the gold standard approach used herein is excellent in predicting/estimating dry weights, the technique suffers from the practical problem that it requires the performance of bioimpedance measurements throughout a dialysis session. As will now be shown, the techniques of the present disclosure overcome this problem and allow as little as one bioimpedance measurement at essentially any time to be used to accurately predict/estimate dry weight.

Table 1 shows the experimental data employed. Twenty-seven patients were randomly divided into two groups, the first group having twelve patients and the second fifteen. For the second group, gold standard determinations of dry weight were obtained, as well as WT and ΔnRho values at the end of dialysis sessions where the gold standard dry weight had been achieved. A least squares regression was then performed by fitting Eq. (7a) to that data to obtain α and β values. That is, the patients in the second group provided "learning" data for the prediction/estimation technique.

Figure 10:
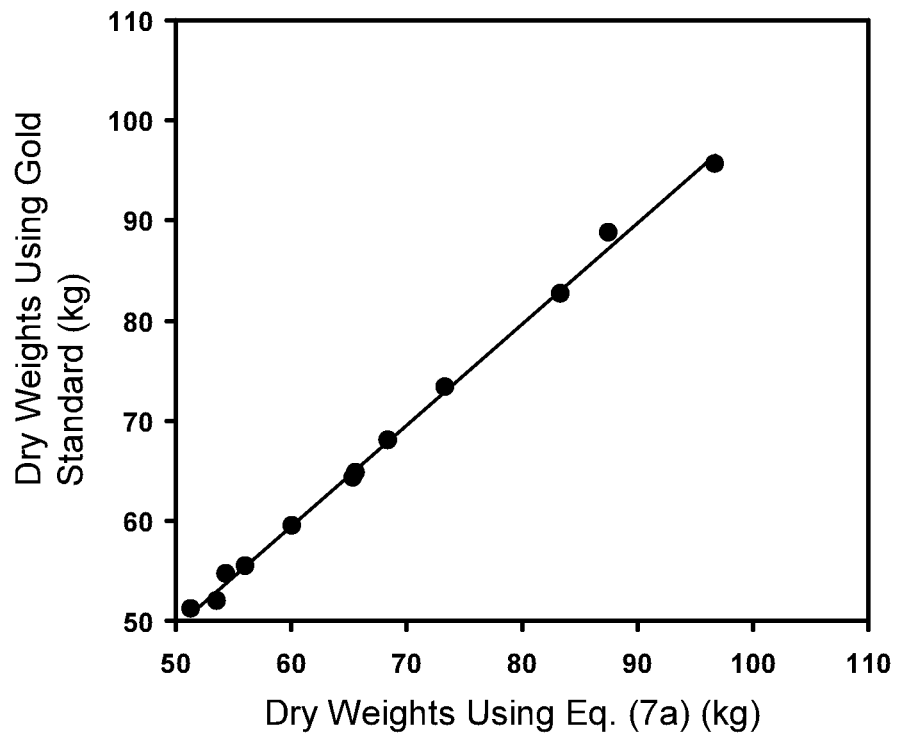
FIG. 10 is a plot comparing the dry weight prediction/estimation techniques disclosed herein (horizontal axis) with the continuous calf bioimpedance spectroscopy technique (gold standard technique) (vertical axis).

The α and β values thus obtained were then used in Eq. (7a), along with WT and ΔnRho measurement, to compute predicted/estimated dry weight (DW) values for the patients in first group. Gold standard dry weight values were also obtained for the patients in the first group. The results are shown in Table 1 and plotted in FIGS. 10 and 11. Specifically, the horizontal axis in FIG. 10 shows the predicted/estimated dry weights in kilograms using Eq. (7a) and the α and β values of 0.5×10$^2$ kilogram$^2$/ohm-meter$^3$ and 0.84 kilograms, respectively, and the vertical axis shows the gold standard dry weight, again in kilograms. The slanted line (essentially at 45°) in FIG. 10 is a least squares fit to the data points and has a slope of 0.9499 and an intercept of 4.177 kilograms. The $R^2$ value for the fit was 0.9891, an exceeding high value for a biological system.

Figure 11:
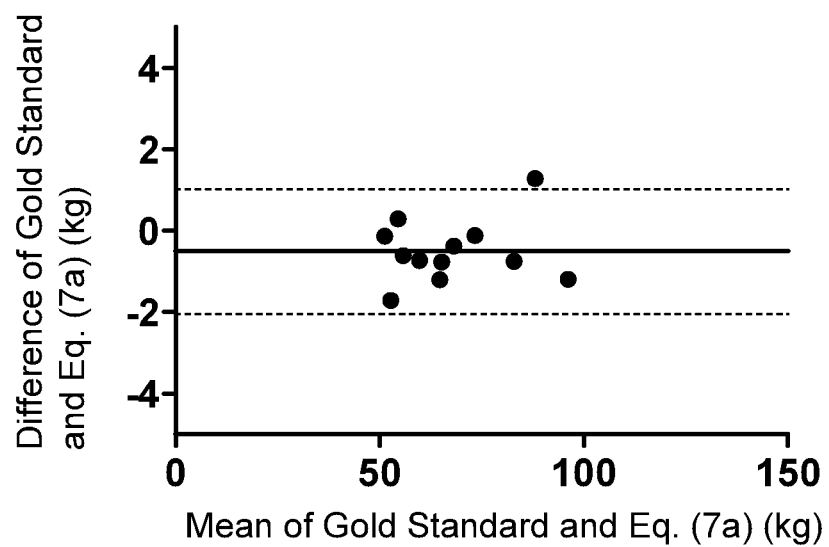
FIG. 11 is a Bland-Altman plot for the data of FIG. 10.

FIG. 11 is a Bland-Altman plot of the same data, where the horizontal axis plots the mean of the gold standard and Eq. (7a) values in kilograms and the vertical axis plots their difference, again in kilograms. The dotted lines represent the average difference±1.96 standard deviations of the difference. Specifically, in FIG. 11, the average difference was −0.5 kilograms and the standard deviation was 0.78 kilograms. As FIGS. 10 and 11 demonstrate, the correlation between the Eq. (7a) values and the gold standard values was excellent.

Figure 12:
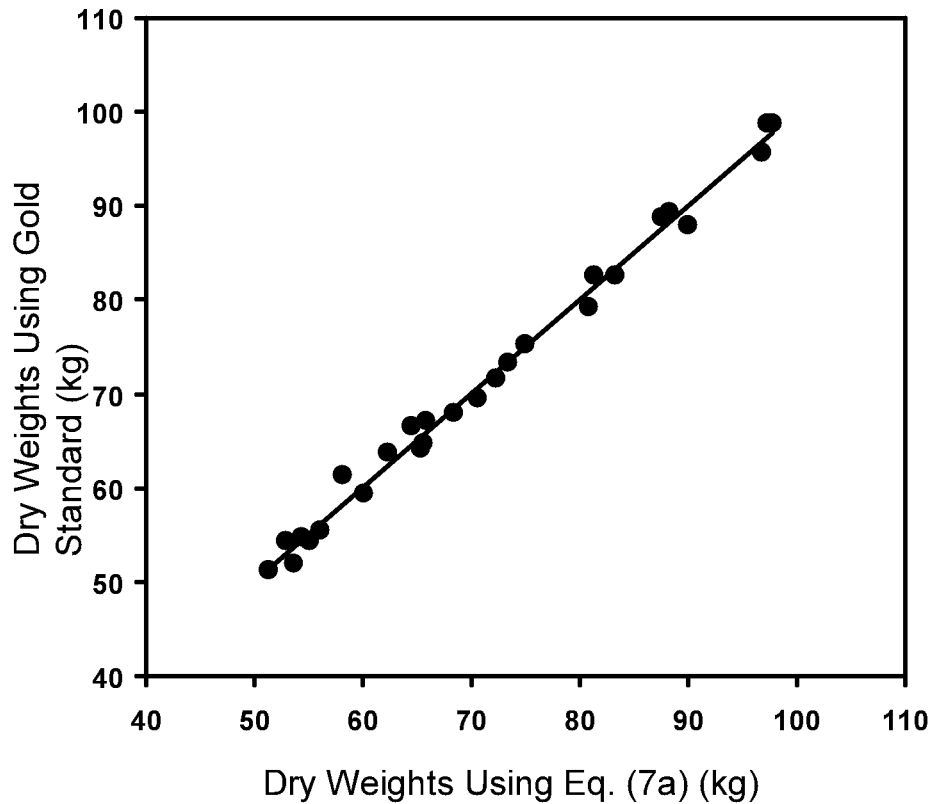
FIG. 12 is a further plot comparing the dry weight prediction/estimation techniques disclosed herein (horizontal axis) with the gold standard technique (vertical axis).
Figure 13:
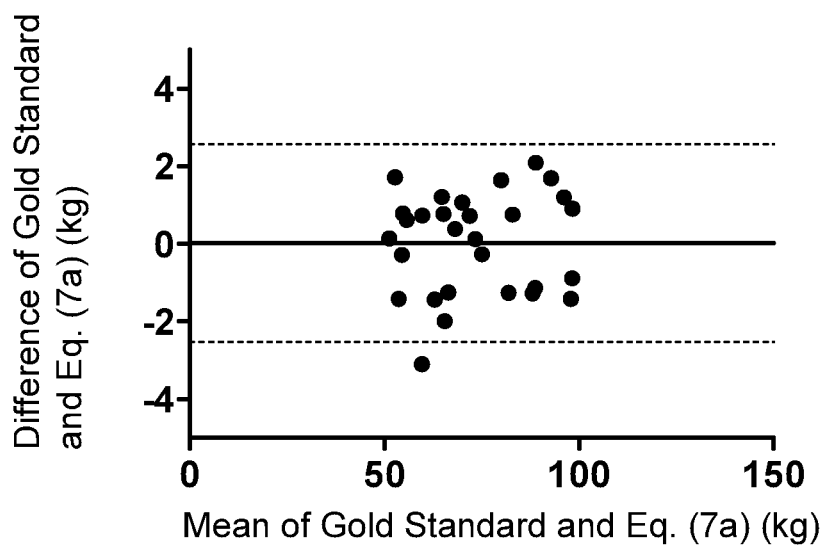
FIG. 13 is a Bland-Altman plot for the data of FIG. 12.

FIGS. 12 and 13 follow the same format as FIGS. 10 and 11, but rather than using just the patients of the first group, these figures use the data for all 27 patients. The least-squares line in FIG. 12 has a slope of 0.9983 and an intercept of 0.1916. The $R^2$ value in this case was 0.9922. The average value of the difference in the Bland-Altman plot of FIG. 13 was 0.025 kilograms and the standard deviation was 1.3 kilograms.

Figure 14:
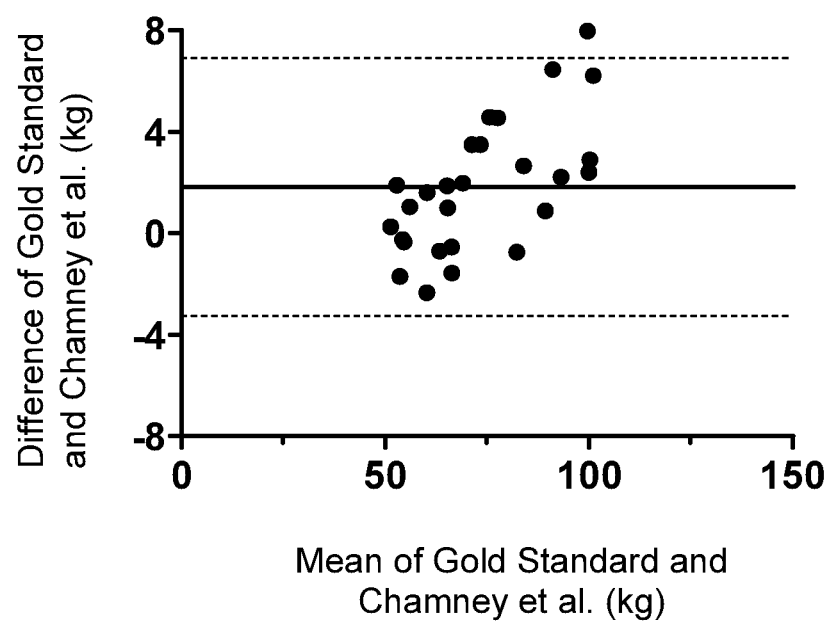
FIG. 14 is a Bland-Altman plot for a comparison between a whole body bioimpedance technique for predicting/estimating dry weight and the gold standard technique.

FIG. 14 is a Bland-Altman plot for a similar experiment employing the gold standard technique and a whole body technique of the type described in Chamney et al., "A whole-body model to distinguish excess fluid from the hydration of major body tissues," *Am J Clin Nutr*, 2007, 85:80-89. The average value of the difference in this case was 1.83 kilograms and the standard deviation was 2.6 kilograms. The superiority of the calf bioimpedance procedure of the present disclosure is evident from this data.

Figure 15:
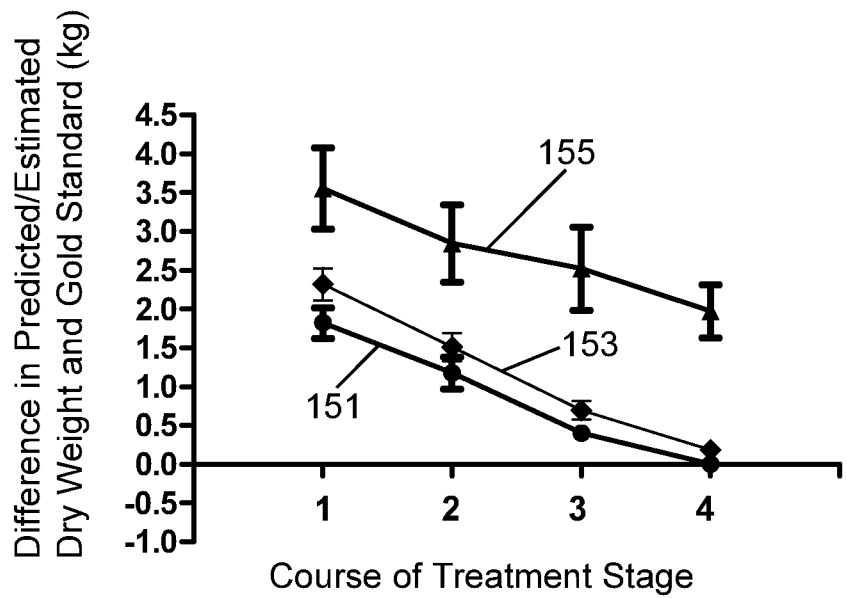
FIGS. 15 and 16 are graphs which compare the dry weight prediction/estimation techniques disclosed herein with a whole body bioimpedance technique. The vertical axis in each figure shows the difference in kilograms between the predicted/estimated dry weight value and the gold standard value. The horizontal axis shows four stages of a dialysis treatment regime beginning with the subject's baseline hydration (stage 1) and ending with the achievement of the gold standard dry weight (stage 4). The same data is plotted in each figure, with FIG. 15 showing standard deviations and FIG. 16 showing mean values.
Figure 16:
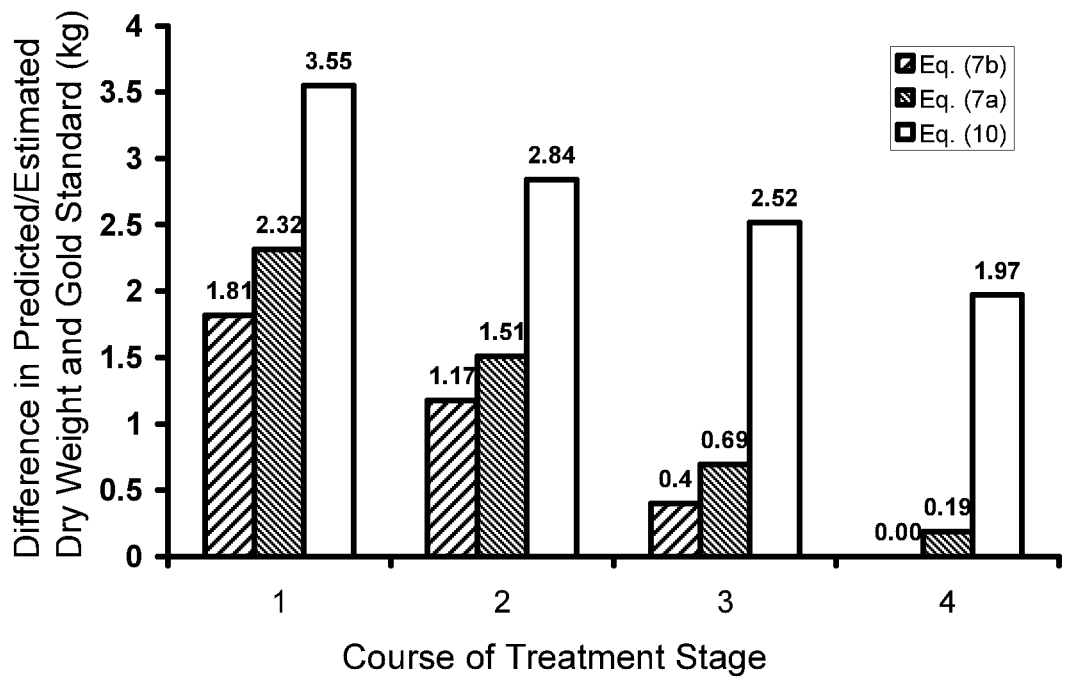

FIGS. 15 and 16 illustrate the ability of Eq. (7b) to predict/estimate dry weight for patients undergoing dialysis. This analysis was performed on a subset of the patients of Table 1, i.e., a subset consisting of nine patients. Fitting of Eq. (7b) to the gold standard data was performed in the same manner as described above in connection with Eq. (7a). Specifically, as noted above, using the gold standard data for the nine patients, $\lambda$ and $\xi$ values of $0.4 \times 10^2$ kilograms$^2$/ohm-meter$^3$ and ⅓ were determined. In addition to the $\lambda$ and $\xi$ values, $\alpha$ and $\beta$ values for Eq. (7b) were also determined for the nine-member population, i.e., $\alpha$ and $\beta$ values of $0.2 \times 10^2$ kilogram$^2$/ohm-meter$^3$ and 0.4 kilograms, respectively (see above). Finally, an analysis using the Chamney et al. whole body technique referenced above was performed using the equation:

$$EFV_{WBM} = 1.136 \cdot wECV - 0.43 \cdot wICV - 0.114 \cdot BW$$

where $EFV_{WBM}$, wECV, wICV, and BW were as defined in Chamney et al., and a dry weight (DW) value was obtained from the equation:

$$DW = WT - EFV_{WBM}. \quad \text{Eq. (10)}$$

The course of treatment from baseline hydration through to dry weight was divided into four stages, with baseline being stage 1 and dry weight, stage 4. Curve 151 of FIG. 15 plots the difference in kilograms between the predicted/estimated dry weight of Eq. (7b) and the gold standard dry weight for the four stages, while curves 153 and 155 show the differences for Eqs. (7a) and (10), respectively. FIG. 16 replots the same data in column form so as to better illustrate the magnitudes of the differences in estimated/predicted dry weight. As can be seen from these figures, Eqs. (7a) and (7b) clearly outperform Eq. (10), with Eq. (7b) being better than Eq. (7a) at each of the four phases.

The mathematical procedures described above can be readily implemented using a variety of computer equipment and a variety of programming languages or mathematical computation packages such as EXCEL (Microsoft Corporation, Redmond, Wash.), MATHEMATICA (Wolfram Research, Champaign, Ill.), MATLAB (MathWorks of Natick, Mass.), or the like. Output from the procedures can be in electronic and/or hard copy form, and can be displayed in a variety of formats, including in tabular and graphical form. Software embodiments of the procedures described herein can be stored and/or distributed in a variety of forms, e.g., on a hard drive, diskette, CD, flash drive, etc. The software can operate on various computing platforms, including personal computers, workstations, mainframes, etc.

Based on the foregoing, the disclosure includes, but is not limited to, the following features/embodiments. The individual features/embodiments, as well as their various paragraphs and subparagraphs, can be used in any and all combinations. As just one example, the computer program of Feature/Embodiment 24 can be programmed to perform any of the methods which proceed it, i.e., any of Features/Embodiments 1-17. Further combinations of these and other types will be evident to persons skilled in the art from the present disclosure.

1. A method of predicting/estimating an individual's dry weight, said individual having a BMI value, comprising:
    (a) obtaining a measured value indicative of the extracellular fluid volume of the individual's calf using a bioimpedance measurement technique;
    (b) obtaining a measured value indicative of the circumferential size C of the individual's calf;
    (c) determining a normalized value indicative of the extracellular fluid volume of the individual's calf from the measured values of steps (a) and (b) and the individual's BMI value;
    (d) determining a difference value between the normalized value of step (c) and a reference value for the normalized value; and
    (e) using the difference value of step (d) to determine a predicted/estimated value for the individual's dry weight.
2. The method of Feature/Embodiment 1 wherein the measured value of step (a) is a resistance value.
3. The method of Feature/Embodiment 2 wherein the resistance value is obtained at a frequency of 5 kilohertz.
4. The method of Feature/Embodiment 1 wherein in step (b), the measured value indicative of the circumference size C of the individual's calf is obtained using a pressure cuff controlled by a tension sensor.
5. The method of Feature/Embodiment 1 wherein step (c) comprises dividing the measured value of step (a) by the individual's BMI value.
6. The method of Feature/Embodiment 1 wherein:
    (i) the bioimpedance measurement technique employs recording electrodes separated by a distance L; and
    (ii) step (c) comprises multiplying the measured value of step (a) by $C^2$ and dividing it by $4\pi L$ times the BMI value.
7. The method of Feature/Embodiment 1 wherein the reference value used in step (d) is obtained by performing steps (a) through (c) on at least one set of reference individuals.
8. The method of Feature/Embodiment 7 wherein the reference individuals are normal subjects.
9. The method of Feature/Embodiment 1 wherein the reference value used in step (d) is determined based on at least one characteristic of the individual.
10. The method of Feature/Embodiment 9 wherein the at least one characteristic of the individual comprises the individual's sex.
11. The method of Feature/Embodiment 9 wherein the at least one characteristic of the individual comprises the individual's obesity.
12. The method of Feature/Embodiment 1 wherein the measured value of step (a) is a resistance value, the normalized value of step (c) is a resistivity value divided by the individual's BMI, and step (e) comprises evaluating an equation of the form:

$$DW=WT-\{\alpha(K-\rho_N)+\beta\}$$

where DW is the predicted/estimated dry weight, WT is the individual's weight at the time steps (a) and (b) are performed, $\rho_N$ is the normalized value of step (c), K is the reference value of step (d), and $\alpha$ and $\beta$ are constants.

13. The method of Feature/Embodiment 12 wherein $\alpha$ and $\beta$ are determined by a fitting procedure using dry weight values determined by a gold standard technique.

14. The method of Feature/Embodiment 1 wherein the measured value of step (a) is a resistance value, the normalized value of step (c) is a resistivity value divided by the individual's BMI, and step (e) comprises evaluating an equation of the form:

$$DW=WT-\lambda \cdot \exp[(100 \cdot (K-\rho_N)/(\text{ohm-meter}^3/\text{kilogram}))^\xi]$$

where DW is the predicted/estimated dry weight, WT is the individual's weight at the time steps (a) and (b) are performed, $\rho_N$ is the normalized value of step (c), K is the reference value of step (d), $\rho_N$ and K are in ohm-meter$^3$/kilogram, and $\lambda$ and $\xi$ are constants.

15. The method of Feature/Embodiment 14 wherein $\lambda$ and $\xi$ are determined by a fitting procedure using dry weight values determined by a gold standard technique.

16. The method of Feature/Embodiment 1 where the individual suffers from one or more of heart failure, liver failure, malnutrition, venous thrombosis, chronic kidney failure, or acute kidney failure.

17. The method of Feature/Embodiment 1 wherein the predicted/estimated dry weight is used to determine the dosage of a medicament.

18. The method of Feature/Embodiment 17 wherein the medicament is a diuretic or a calcium channel blocker.

19. A medicament to be administered to a patient wherein the dosage and/or the administration scheme of the medicament is determined at least in part based on a dry weight that is predicted/estimated according to the method of Feature/Embodiment 1.

20. The medicament of Feature/Embodiment 19 wherein the medicament is a diuretic or a calcium channel blocker.

21. A diet to be administered to a patient wherein the diet is determined at least in part based on a dry weight that is predicted/estimated according to the method of Feature/Embodiment 1.

22. The diet of Feature/Embodiment 21 wherein the diet is a low sodium diet.

23. Apparatus comprising a computer system which has been programmed to:
  (i) receive inputs regarding the bioimpedance and circumference measurements of steps (a) and (b) of Feature/Embodiment 1; and
  (ii) perform steps (c) through (e) of Feature/Embodiment 1 using those inputs.

24. An article of manufacture comprising a non-transitory computer readable storage medium having computer executable code embodied therein for performing steps (c) through (e) of Feature/Embodiment 1.

25. A computer program comprising instructions which, when executed by a computer, cause the computer to execute a method according to Feature/Embodiment 1.

26. A method for establishing a target dry weight for an individual, said individual having a BMI value, comprising:
  (a) obtaining a measured resistance value R indicative of the extracellular fluid volume of the individual's calf using a bioimpedance measurement technique;
  (b) obtaining a measured value indicative of the circumferential size C of the individual's calf;
  (c) determining a normalized resistivity value $\rho_N$ indicative of the extracellular fluid volume of the individual's calf from the measured values of steps (a) and (b), the individual's BMI value, and an equation of the form:

$$\rho_N=R \cdot C^2/(4\pi L \cdot \text{BMI});$$

(d) determining a difference value $\Delta nRho$ between the normalized value $\rho_N$ of step (c) and a reference value K for the normalized value using an equation of the form:

$$\Delta nRho=-(\rho_N-K); \text{ and}$$

(e) using the difference value of step (d) to determine the target dry weight;
  wherein the target dry weight TDW satisfies the equation:

$$WT-(\alpha \cdot \Delta nRho+\beta)-1.0$$

$$\leq TDW \leq$$

$$WT-(\alpha \cdot \Delta nRho+\beta)+1.0$$

where the equation is in kilograms, WT is the individual's weight at the time steps (a) and (b) are performed, and $\alpha$ and $\beta$ are predetermined constants.

27. The method of Feature/Embodiment 26 wherein the reference value used in step (d) is obtained by performing steps (a) through (c) on at least one set of reference individuals.

28. The method of Feature/Embodiment 27 wherein the reference individuals are normal subjects.

29. The method of Feature/Embodiment 26 wherein the reference value used in step (d) is determined based on at least one characteristic of the individual.

30. The method of Feature/Embodiment 29 wherein the at least one characteristic of the individual comprises the individual's sex.

31. The method of Feature/Embodiment 29 wherein the at least one characteristic of the individual comprises the individual's obesity.

32. The method of Feature/Embodiment 26 wherein a and 13 are determined by a fitting procedure using dry weight values determined by a gold standard technique.

33. The method of Feature/Embodiment 26 where the individual suffers from one or more of heart failure, liver failure, malnutrition, venous thrombosis, chronic kidney failure, or acute kidney failure.

34. The method of Feature/Embodiment 26 wherein the target dry weight is used to determine the dosage of a medicament.

35. The method of Feature/Embodiment 34 wherein the medicament is a diuretic or a calcium channel blocker.

36. A medicament to be administered to a patient wherein the dosage and/or the administration scheme of the medicament is determined at least in part based on a target dry weight established according to the method of Feature/Embodiment 26.

37. The medicament of Feature/Embodiment 36 wherein the medicament is a diuretic or a calcium channel blocker.

38. A diet to be administered to a patient wherein the diet is determined at least in part based on a target dry weight established according to the method of Feature/Embodiment 26.

39. The diet of Feature/Embodiment 38 wherein the diet is a low sodium diet.

40. Apparatus comprising a computer system which has been programmed to:
   (i) receive inputs regarding the bioimpedance and circumference measurements of steps (a) and (b) of Feature/Embodiment 26; and
   (ii) perform steps (c) through (e) of Feature/Embodiment 26 using those inputs.

41. An article of manufacture comprising a non-transitory computer readable storage medium having computer executable code embodied therein for performing steps (c) through (e) of Feature/Embodiment 26.

42. A computer program comprising instructions which, when executed by a computer, cause the computer to execute a method according to Feature/Embodiment 26.

43. A method for establishing a target dry weight for an individual, said individual having a BMI value, comprising:
   (a) obtaining a measured resistance value R indicative of the extracellular fluid volume of the individual's calf using a bioimpedance measurement technique;
   (b) obtaining a measured value indicative of the circumferential size C of the individual's calf;
   (c) determining a normalized resistivity value $\rho_N$ indicative of the extracellular fluid volume of the individual's calf from the measured values of steps (a) and (b), the individual's BMI value, and an equation of the form:

$$\rho_N = R \cdot C^2 / (4\pi L \cdot \text{BMI});$$

(d) determining a difference value $\Delta nRho$ between the normalized value $\rho_N$ of step (c) and a reference value K for the normalized value using an equation of the form:

$$\Delta nRho = -(\rho_N - K);\text{ and}$$

(e) using the difference value of step (d) to determine the target dry weight;
   wherein the target dry weight TDW satisfies the equation:

$$WT - \lambda \cdot \exp[(100 \cdot \Delta nRho / (\text{ohm-meter}^3/\text{kilogram}))^\xi] - 1.0$$

$$\leq TDW \leq$$

$$WT - \lambda \cdot \exp[(100 \cdot \Delta nRho / (\text{ohm-meter}^3/\text{kilogram}))^\xi] + 1.0$$

where the equation is in kilograms, WT is the individual's weight at the time steps (a) and (b) are performed, $\rho_N$ and K are in ohm-meter$^3$/kilogram, and $\lambda$ and $\xi$ are constants.

44. The method of Feature/Embodiment 43 wherein the reference value used in step (d) is obtained by performing steps (a) through (c) on at least one set of reference individuals.

45. The method of Feature/Embodiment 44 wherein the reference individuals are normal subjects.

46. The method of Feature/Embodiment 43 wherein the reference value used in step (d) is determined based on at least one characteristic of the individual.

47. The method of Feature/Embodiment 46 wherein the at least one characteristic of the individual comprises the individual's sex.

48. The method of Feature/Embodiment 46 wherein the at least one characteristic of the individual comprises the individual's obesity.

49. The method of Feature/Embodiment 43 wherein $\lambda$ and $\xi$ are determined by a fitting procedure using dry weight values determined by a gold standard technique.

50. The method of Feature/Embodiment 43 where the individual suffers from one or more of heart failure, liver failure, malnutrition, venous thrombosis, chronic kidney failure, or acute kidney failure.

51. The method of Feature/Embodiment 43 wherein the target dry weight is used to determine the dosage of a medicament.

52. The method of Feature/Embodiment 51 wherein the medicament is a diuretic or a calcium channel blocker.

53. A medicament to be administered to a patient wherein the dosage and/or the administration scheme of the medicament is determined at least in part based on a target dry weight established according to the method of Feature/Embodiment 43.

54. The medicament of Feature/Embodiment 53 wherein the medicament is a diuretic or a calcium channel blocker.

55. A diet to be administered to a patient wherein the diet is determined at least in part based on a target dry weight established according to the method of Feature/Embodiment 43.

56. The diet of Feature/Embodiment 55 wherein the diet is a low sodium diet.

57. Apparatus comprising a computer system which has been programmed to:
   (i) receive inputs regarding the bioimpedance and circumference measurements of steps (a) and (b) of Feature/Embodiment 43; and
   (ii) perform steps (c) through (e) of Feature/Embodiment 43 using those inputs.

58. An article of manufacture comprising a non-transitory computer readable storage medium having computer executable code embodied therein for performing steps (c) through (e) of Feature/Embodiment 43.

59. A computer program comprising instructions which, when executed by a computer, cause the computer to execute a method according to Feature/Embodiment 43.

60. A method for reducing the fluid overload of an individual, said individual having a BMI value, comprising:
   (a) obtaining a measured value indicative of the extracellular fluid volume of the individual's calf using a bioimpedance measurement technique;
   (b) obtaining a measured value indicative of the circumferential size C of the individual's calf;
   (c) determining a normalized value indicative of the extracellular fluid volume of the individual's calf from the measured values of steps (a) and (b) and the individual's BMI value;
   (d) determining a difference value between the normalized value of step (c) and a reference value for the normalized value;
   (e) using the difference value of step (d) to determine a predicted/estimated value for the individual's dry weight; and
   (f) reducing the fluid overload of the individual based at least in part on the predicted/estimated dry weight.

61. Medicament for use in a method for reducing the fluid overload of an individual, the method comprising the following steps:

(a) obtaining a measured value indicative of the extracellular fluid volume of the individual's calf using a bioimpedance measurement technique;
(b) obtaining a measured value indicative of the circumferential size C of the individual's calf;
(c) determining a normalized value indicative of the extracellular fluid volume of the individual's calf from the measured values of steps (a) and (b) and the individual's BMI value;
(d) determining a difference value between the normalized value of step (c) and a reference value for the normalized value;
(e) using the difference value of step (d) to determine a predicted/estimated value for the individual's dry weight; and
(f) reducing the fluid overload of the individual by determining the dosage and/or the administration scheme of the medicament at least in part based on the predicted/estimated dry weight.

62. The medicament of Feature/Embodiment 61 where the medicament is a diuretic.

A variety of modifications that do not depart from the scope and spirit of the invention will be evident to persons of ordinary skill in the art from the foregoing disclosure. Particularly, gold standard techniques other than the one discussed above and illustrated in FIGS. 5-9, can be used in determining fitting coefficients. And, of course, more (or less) individuals can be used in the fitting process, as desired. The following claims are intended to cover the specific embodiments set forth herein as well as modifications, variations, and equivalents of those embodiments of the foregoing and other types.

TABLE 1

| Patient | Sex | Age (years) | Height (cm) | Weight (kg) | Gold Standard DW (g) | Predicted DW (kg) |
|---|---|---|---|---|---|---|
| 1 | F | 72 | 166 | 57.8 | 55.5 | 56.1 |
| 2 | M | 74 | 153 | 71.5 | 68.0 | 68.4 |
| 3 | F | 55 | 165 | 90.9 | 88.8 | 87.5 |
| 4 | M | 42 | 174 | 67.0 | 64.8 | 65.6 |
| 5 | F | 61 | 164 | 53.1 | 51.2 | 51.3 |
| 6 | F | 45 | 159 | 98.9 | 95.6 | 96.8 |
| 7 | M | 66 | 157 | 56.9 | 51.9 | 53.6 |
| 8 | M | 34 | 164 | 60.6 | 59.4 | 60.1 |
| 9 | M | 62 | 180 | 67.4 | 64.2 | 65.4 |
| 10 | F | 54 | 154 | 74.8 | 73.3 | 73.4 |
| 11 | M | 64 | 183 | 84.8 | 82.6 | 83.4 |
| 12 | M | 51 | 162 | 56.9 | 54.7 | 54.4 |
| 13 | F | 56 | 162 | 99.5 | 98.7 | 97.3 |
| 14 | M | 68 | 164 | 67.2 | 66.5 | 64.5 |
| 15 | F | 61 | 162 | 56.5 | 54.4 | 55.2 |
| 16 | M | 52 | 176 | 68.8 | 67.1 | 65.8 |
| 17 | M | 66 | 185 | 61.9 | 61.3 | 58.2 |
| 18 | F | 49 | 162 | 83.7 | 82.6 | 81.3 |
| 19 | M | 42 | 178 | 73.8 | 71.6 | 72.3 |
| 20 | M | 57 | 173 | 91.5 | 87.9 | 90.0 |
| 21 | M | 26 | 175 | 75.9 | 75.3 | 75.0 |
| 22 | F | 63 | 174 | 64.2 | 63.7 | 62.3 |
| 23 | M | 46 | 166 | 100.3 | 98.7 | 97.8 |
| 24 | M | 44 | 175 | 73.6 | 69.5 | 70.6 |
| 25 | F | 57 | 146 | 54.6 | 54.4 | 53.0 |
| 26 | M | 61 | 177 | 90.0 | 89.4 | 88.3 |
| 27 | F | 39 | 155 | 83.0 | 79.2 | 80.8 |

What is claimed is:

1. A method for administering a dosage of a medicament to a user having a body mass index value including a bioimpedance measurement system, the bioimpedance measurement system comprising a central processing unit, a stimulating system including stimulating electrodes, and a recording system including recording electrodes, the method comprising:
    determining a resistance value of extracellular fluid volume of a user's calf by the stimulating and recording electrodes, the resistance value being sent to the central processing unit;
    measuring a circumference of the user's calf by the stimulating and recording electrodes, the circumference measurement being sent to the central processing unit;
    the central processing unit calculating a normalized resistivity based on the resistance value, the circumference measurement, and a body mass index value of the user;
    the central processing unit calculating an offset value between the normalized resistivity and a reference value for the normalized resistivity;
    the central processing unit calculating an estimated dry weight of the user, the estimated dry weight being based on the offset value, and a weight of the user determined during the calculation of the offset value is different from the estimated dry weight;
    determining a dosage of a medicament based on utilizing the estimated dry weight to determine a dosage of a medicament; and
    administrating the dosage of the medicament to the user.

2. The method of claim 1, wherein the reference value is obtained by determining the resistance value of extracellular fluid volume of the user's calf and measuring the circumference of the user's calf on at least one set of reference individuals.

3. The method of claim 2, wherein the reference individuals are healthy subjects.

4. The method of claim 1, wherein the resistance value is determined by the extracellular fluid volume of the user's calf, the normalized resistivity is a resistivity value divided by the user's body mass index value, and calculating the estimated dry weight comprises evaluating an equation of the form:

$$DW = WT \cdot \{\alpha \cdot (K - \rho N) + \beta\},$$

wherein DW is the estimated dry weight, WT is the user's weight at the time the resistance value of extracellular fluid volume of the user's calf is determined and the circumference of the user's calf is measured, $\rho N$ is the normalized value, K is the reference value, and $\alpha$ and $\beta$ are constants.

5. The method of claim 4, wherein $\alpha$ and $\beta$ are determined by a fitting procedure using dry weight obtained from bioimpedance spectroscopy measurements of a population of hemodialysis patients as they are undergoing hemodialysis treatment.

6. The method of claim 1, wherein the resistance value is determined by the extracellular fluid volume of the user's calf, the normalized resistivity is a resistivity value divided by the user's body mass index value, and calculating the estimated dry weight comprises evaluating an equation of the form:

$$DW = WT - \lambda \cdot \exp[(100 \cdot (K - \rho N)/(\text{ohm-meter}^3/\text{kilogram}))^\xi],$$

wherein DW is the estimated dry weight, WT is the user's weight at the time the resistance value of extracellular fluid volume of the user's calf is determined and the circumference of the user's calf is measured, $\rho_N$ is the normalized value, K is the reference value, $\rho_N$ and K are in ohm-meter$^3$/kilogram, and $\lambda$ and $\xi$ are constants.

7. The method of claim 6, wherein $\lambda$ and $\xi$ are determined by a fitting procedure using dry weight values obtained from bioimpedance spectroscopy measurements of a population of hemodialysis patients as they are undergoing hemodialysis treatment.

8. The method of claim 1, the medicament comprising at least one of a diuretic or a calcium channel blocker.

9. A method for controlling fluid overload of a patient, the method comprising:
receiving a resistance value of extracellular fluid volume of the patient's calf determined by stimulating electrodes and recording electrodes of a bioimpedance measurement system;
receiving a circumference of the patient's calf determined by the stimulating and recording electrodes;
calculating a normalized resistivity based on the resistance value, the circumference measurement, and a body mass index value of the patient;
calculating an offset value between the normalized resistivity and a reference value for the normalized resistivity;
calculating an estimated dry weight of the patient, the estimated dry weight being based on the offset value, and a weight of the patient determined during the calculation of the offset value is different from the estimated dry weight;
determining a dosage of a medicament to reduce fluid overload of the patient based on the estimated dry weight; and
administrating the dosage of the medicament to the patient.

10. The method of claim 9, wherein the reference value is obtained by determining the resistance value of extracellular fluid volume of the patient's calf and measuring the circumference of the patient's calf on at least one set of reference individuals.

11. The method of claim 10, wherein the reference individuals are healthy subjects.

12. The method of claim 9, wherein the resistance value is determined by the extracellular fluid volume of the patient's calf, the normalized resistivity is a resistivity value divided by the patient's body mass index value, and calculating the estimated dry weight comprises evaluating an equation of the form:

$$DW=WT-\{\alpha\cdot(K-\rho N)+\beta\},$$

wherein DW is the estimated dry weight, WT is the patient's weight at the time the resistance value of extracellular fluid volume of the patient's calf is determined and the circumference of the patient's calf is measured, $\rho N$ is the normalized value, K is the reference value, and $\alpha$ and $\beta$ are constants.

13. The method of claim 12, wherein $\alpha$ and $\beta$ are determined by a fitting procedure using dry weight obtained from bioimpedance spectroscopy measurements of a population of hemodialysis patients as they are undergoing hemodialysis treatment.

14. The method of claim 9, wherein the resistance value is determined by the extracellular fluid volume of the patient's calf, the normalized resistivity is a resistivity value divided by the patient's body mass index value, and calculating the estimated dry weight comprises evaluating an equation of the form:

$$DW=WT-\lambda\cdot\exp[(100\cdot(K-\rho N)/(\text{ohm-meter}^3/\text{kilogram}))^{\xi}],$$

wherein DW is the estimated dry weight, WT is the patient's weight at the time the resistance value of extracellular fluid volume of the patient's calf is determined and the circumference of the patient's calf is measured, $\rho_N$ is the normalized value, K is the reference value, $\rho_N$ and K are in ohm-meter$^3$/kilogram, and $\lambda$ and $\xi$ are constants.

15. The method of claim 14, wherein $\lambda$ and $\xi$ are determined by a fitting procedure using dry weight values obtained from bioimpedance spectroscopy measurements of a population of hemodialysis patients as they are undergoing hemodialysis treatment.

16. The method of claim 9, the medicament comprising at least one of a diuretic or a calcium channel blocker.

17. A method for administering a dosage of a medicament to a patient, the method comprising:
determining a dry weight of the patient via a computing system comprising a central processing unit and a non-transitory computer readable storage medium having computer executable code embodied therein which, when executed by the central processing unit, causes the central processing unit to perform a process for determining a dosage of a medicament to the patient having a body mass index value, the process comprising, via the central processing unit:
receiving a resistance value of extracellular fluid volume of the patient's calf determined by stimulating and recording electrodes of a bioimpedance measurement system communicatively coupled to the central processing unit, the bioimpedance measurement unit comprising a stimulating system having the stimulating electrodes and a recording system having the recording electrodes,
receiving a circumference of the patient's calf determined by the stimulating and recording electrodes,
calculating a normalized resistivity based on the resistance value, the circumference measurement, and a body mass index value of the patient,
calculating an offset value between the normalized resistivity and a reference value for the normalized resistivity,
calculating an estimated dry weight of the patient, the estimated dry weight being based on the offset value, and a weight of the patient determined during the calculation of the offset value is different from the estimated dry weight, and
determining a dosage of a medicament based on utilizing the estimated dry weight to determine a dosage of a medicament; and
administrating the dosage of the medicament to the patient.

18. The method of claim 17, wherein the resistance value is determined by the extracellular fluid volume of the patient's calf, the normalized resistivity is a resistivity value divided by the patient's body mass index value, and calculating the estimated dry weight comprises evaluating an equation of the form:

$$DW=WT-\{\alpha\cdot(K-\rho N)+\beta\},$$

wherein DW is the estimated dry weight, WT is the patient's weight at the time the resistance value of extracellular fluid volume of the patient's calf is determined and the circumference of the patient's calf is measured, $\rho N$ is the normalized value, K is the reference value, and $\alpha$ and $\beta$ are constants.

19. The method of claim 17, wherein the resistance value is determined by the extracellular fluid volume of the patient's calf, the normalized resistivity is a resistivity value divided by the patient's body mass index value, and calculating the estimated dry weight comprises evaluating an equation of the form:

$$DW = WT - \lambda \cdot \exp[(100 \cdot (K - \rho_N)/(\text{ohm-meter}^3/\text{kilogram}))^\xi],$$

wherein DW is the estimated dry weight, WT is the patient's weight at the time the resistance value of extracellular fluid volume of the patient's calf is determined and the circumference of the patient's calf is measured, $\rho_N$ is the normalized value, K is the reference value, $\rho_N$ and K are in ohm-meter$^3$/kilogram, and $\lambda$ and $\xi$ are constants.

20. The method of claim 17, the medicament comprising at least one of a diuretic or a calcium channel blocker.

* * * * *